(12) United States Patent
Forssmann et al.

(10) Patent No.: US 8,106,061 B2
(45) Date of Patent: Jan. 31, 2012

(54) USE OF PHOSPHODIESTERASE INHIBITORS IN THE TREATMENT OF PROSTATIC DISEASES

(75) Inventors: Wolf-Georg Forssmann, Hannover (DE); Christian Georg Stief, Hemmingen (DE); Michael Carsten Truss, Hannover (DE); Stefan Uckert, Garbsen (DE); Udo Jonas, Hannover (DE)

(73) Assignee: Uropep Biotech GBR, Garbsen (DE)

( * ) Notice: Subject to any disclaimer, the term of this patent is extended or adjusted under 35 U.S.C. 154(b) by 157 days.

(21) Appl. No.: 10/443,870

(22) Filed: May 23, 2003

(65) Prior Publication Data

US 2003/0199517 A1 Oct. 23, 2003

Related U.S. Application Data

(63) Continuation of application No. 09/462,090, filed as application No. PCT/EP97/03617 on Jul. 9, 1997, now abandoned.

(51) Int. Cl.
*A61K 31/517* (2006.01)
*A61K 31/519* (2006.01)
*A61K 31/4164* (2006.01)
*A61K 31/357* (2006.01)

(52) U.S. Cl. ............. 514/266.22; 514/261.1; 514/262.1; 514/266.24; 514/396; 514/452

(58) Field of Classification Search ................ 514/261.1, 514/263.22, 248, 266.22, 452, 266.24, 262.1, 514/400, 456
See application file for complete search history.

(56) References Cited

U.S. PATENT DOCUMENTS

| | | | | |
|---|---|---|---|---|
| 5,250,534 A | * | 10/1993 | Bell et al. | 514/252.16 |
| 5,721,238 A | * | 2/1998 | Heiker et al. | 514/266.31 |
| 5,858,694 A | * | 1/1999 | Piazza et al. | 435/19 |
| 6,207,666 B1 | * | 3/2001 | Piazza et al. | 514/248 |

FOREIGN PATENT DOCUMENTS

| | | | |
|---|---|---|---|
| DE | 195 40 642 | | 5/1997 |
| EP | 0 463 756 | * | 1/1992 |
| WO | 94/28902 | * | 12/1994 |
| WO | 97/05876 | * | 2/1997 |

OTHER PUBLICATIONS

The Merck Index (12th edition) (1996), p. 567.*
Truss et al., Urology, 45(3), (May 1995), pp. 893-901.*
Viggiano et al., Prostaglandins, Leukotrienes and Medicine, 20(1), (Oct. 1985), 89-97.*
Thornbury et al., British Journal of Pharmacology, 116, (1995), 2451-2456.*
Truss et al., Neurology and Urodynamics, 15(1), (1996), 59-70.*
Burnett et al., Urology, (Mar. 1995), 45/3, pp. 435-439.*
Furchgott, R.F., (1988), in Vasodilation: Vascular Smooth Muscle, Peptides and Endothelium (P.M Vanhoutte, ed.), Raven Press, New York, pp. 401-414.*
Takeda et al., Urology, (Mar. 1995), 45/3, pp. 440-446.*
Boolell et al. Br. J. Urol., Aug. 1996, vol. 78, No. 2, pp. 257-261 (Absract attached).*
Taddei et al. American Journal of Hypertension, 1992, vol. 5, pp. 29-31 (Abstract attached).*
Singh et al. J. Cancer Res. Clin. Oncol., 1992, vol. 119, No. 2, pp. 117-120 (Abstract attached).*
Schou et al. Scand. J. Urol. Nephrol. Suppl., 1996, vol. 179, pp. 119-122 (Abstract attached).*
Afzal et al., '5-HT$_4$-elicited positive intropic response is mediated by cAMP and regulated by PDE3 in failing rat and human cardiac ventricles', British Journal of Pharmacology, 2008, vol. 155, p. 1005-1014.
Anderson et al., 'Effects of phosphodiesterase-5 inhibition by sildenafil in the pressure overloaded right heart', The European Journal of Heart Failure, 2008, vol. 10, p. 1158-1165.
Blander et al., 'Efficacy of sildenafil in erectile dysfunction after radical prostatectomy', International Journal of Impotence Research, 2000, vol. 12, p. 165-168.
Estrade et al. 'Effect of a cGMP-specific phosphodiesterase inhibitor on retinal function', European Journal of Pharmacology, 1998, 352(2-3), p. 157-63.
Gibbs et al., 'Do we still need dipyridamole?', British Journal of Clinical Pharmacology, 1998, vol. 45, p. 323-328.
Hagiware et al., 'Effects of vinpocetine on cyclic nucleotide metabolism in vascular smooth muscle', Biochemical Pharmacology, Feb. 1, 1984, pp. 453-457.
Humphrey et al., 'Improved functional recovery of ischemic myocardium by suppression of adenosine catabolism', Journal of Thorac. Cardiovascular Surgery, 1982, 84: 16-22.

(Continued)

*Primary Examiner* — James D Anderson
(74) *Attorney, Agent, or Firm* — Jacobson Holman, PLLC

(57) ABSTRACT

The present invention pertains to the use of inhibitors of phosphodiesterase I, IV and V for the prophylaxis and treatment of prostatic diseases, in particular the use of
a) 2-(2-propoxy-phenyl)-8-azapurin-6-one (zaprinast);
b) dipyridamole;
c) 1-(3-chlorophenylamino)-4-phenylphthalazine (M5445);
d) 2-(N-(4-carboxypiperidine-6-chloro-4-(3,4-(methylendioxy)benzyl)amino)quinazoline (E 4021, ER 21355);
e) 2,3-dihydro-8-hydroxy-7-nitro-1,4-benzodioxine-2-methanol, alpha-nitrate (E 4701);
f) 4-((3,4-(methylendioxy)benzyl)amino)-6,7,8-trimethoxy-quinazoline;
g) 1-methyl-3-propyl-6-(5-(N-(4-methylmorpholino)sulfonyl)-2-ethoxyphenyl)pyrazole[4,5]pyrimidin-4(5H) one (sildenafil);
i) 1-cyclopentyl-3-methyl-6-(4-pyridinyl)pyrazolo (3,4-d) pyrimidin-4(5H)-one (WIN 58237);
j) 7-(3-(4-acetyl-3-hydroxy-2-propyl-phenoxy)-2-hydroxy-propoxy)-2-carboxy-2,3-didehydro-chronan-4-one (FPL-557212);
k) quinazolines and their trimethoxy derivatives;
l) Pyrazolopyrimidones;
as well as pharmacologically compatible salts thereof, quinazolines and their trimethoxy derivatives, pyrazolopyrimidones or compatible salts thereof, in local and systemic administration.

5 Claims, No Drawings

OTHER PUBLICATIONS

Picano, E. on behalf of the PIS study group, 'Dipyridamole in chronic stable angina pectoris—A randomized, double blind, placebo-controlled, parallel group study', European Heart Journal, 2001, vol. 22, p. 1785-1793.

Podzuweit et al., 'Isozyme selective inhibition of cGMP-stimulated cyclic nucleotide phosphodiesterases by erythro-9-(2-Hydroxy-3-Nonyl) adenine', Cellular Signalling, 1995, vol. 7, p. 733-738.

Szatmari et al., 'Vinpocetine for cognitive impairment and dementia (Review)', The Cochrane Library, The Cochrane Collection, 2009, Issue 3.

Takase et al., 'Cyclic GMP phosphodiesterase inhibitors. 1. The discovery of a novel potent inhibitor, 4-((3,4-(methylenedioxy)benzyl)amino)-6,7,8-trimethoxyquinazoline.', Journal Med. Chem., Nov. 26, 1993, 36(24) p. 3765-70.

Xia et al., 'Synthesis and evaluation of polycyclic pyrazolo[3,4-d]pyramidines as PDE1 and PDE5 cGMP phosphodiesterase inhibitors', Journal Med. Chem, Dec. 19, 1997, 40(26) p. 4372-7.

Zhang, Q. et al., 'Reduction in interaction between cGMP and cAMP in dog ventricular myocytes with hypertrophic failure', American Journal Physiol. Heart Circ. Physiol., 2005, 289:1251-1257.

* cited by examiner

USE OF PHOSPHODIESTERASE INHIBITORS IN THE TREATMENT OF PROSTATIC DISEASES

This is a continuation of application Ser. No. 09/462,090 filed Apr. 6, 2000 now abandoned which is a 371 of application no. PCT/EP97/03617, filed Jul. 9, 1997, and published in German.

The prostate gland is an organ of about chest-nut size which in males surrounds the cervix of the vesical outlet. In 50% of the males in the age of above 50 years, a benign growth of the prostate gland occurs which may result in severe difficulties in the miction up to anuria and which is subject to treatment obligation. Most of the affected patients must be treated with surgical methods.

In the development of benign prostatic hyperplasia (BPH), the glandular portions of the prostate gland increase by double their volume, and the muscular and fibrous portions increase by four times their volume (Christmas and Kirby, W. J. Urol. 9: 36-40, 1991). Since these muscle cells account for a large portion of the total prostatic tissue (at least 35%), a distinct improvement of miction can be achieved by means of a pharmacologically induced relaxation of these muscle cells (Hedlund and Andersson, J. Urol. 130: 275-278, 1983). The substances used to date mostly belong to the group of alpha-receptor blockers (Lepor et al., J. Urol. 143: 267, 1990), or they interfered with the hormonal regulation of the prostate gland (Kirby and Christmas, W. J. Urol., 9: 41-44, 1991); these medicament treatments were characterized by either a very low effectiveness, a slow onset of action, or significant Bide-effects, or a combination of such effects.

Therefore, we have examined a completely different pharmacological principle of action, namely the affection of a key enzyme within the smooth muscle cells of the prostate gland, phosphodiesterase.

The physiological transmission of information for the relaxation of smooth muscle cells is effected by messengers of the blood (hormones) or the nerves (neurotransmitters). These messengers and neurotransmitters cause an increase in the levels of the cyclic nucleotides "cyclic adenosine monophosphate" (cAMP) and "cyclic guanosine monophosphate" (cGMP) in the smooth muscle cell, resulting in relaxation. cAMP and cGMP themselves are hydrolyzed by phosphodiesterases (PDEs). Inhibitors of the PDEs in turn reduce the digestion of cAMP and cGMP, resulting in an increase of these molecules within the cell and thus in a relaxation of the smooth muscle cell. This mechanism of action has been described, for instance, by C. D. Nicholson, R. A. Challiss, and M. Shadid: Trends Pharmacol. Sci., 12 (1991), 19-27, C. D. Nicholson and M. Shadid: Pulm. Pharmacol. 7 (1) (1994), 1-17, and T. J. Torphy et al.: J. Pharmacol. Exp. Ther. 265 (3) (1993), 1213-23.

From these publications as well as from W. J. Thompson: Pharmacol. Ther. 51 (1991), 13-33, and J. Beavo in: J. Beavo and M. D. Housley (eds.): Cyclic nucleotide phosphodiesterases: Structure, regulation and drug action, Chichester, New York-Brisbane-Toronto-Singapore, Wiley, 1990: 3-15, there is further known the distinction of a number of subesterases of PDE, the specific phosphodiesterases (sPDE). There is distinguished between five different sPDEs which are differently distributed in the individual organs and organ systems and exhibit different levels of effectiveness according to their distribution. In the publications mentioned, there is also discussed the occurrence of the different isoenzymes in various tissues.

An interesting target for the use of PDE isoenzyme selective inhibitors is the lower urinary tract since the medicamental therapy of prostate dysfunctions with conventional substances is often little effective and full of side-effects. Therefore, a well-aimed affection of the prostatic muscles by inhibiting a functionally important sPDE isoenzyme appears to be superior to conventional therapy methods.

Surprisingly, it has now been found that sPDE I, sPDE IV and sPDE V are of particular importance in human prostatic muscles: After performing Q-sepharose chromatography, there has been found a typical pattern of the human prostatic tissue showing the presence of the PDE isoforms I, IV and V (FIG. 1). A well-aimed inhibition of these isoenzymes will result in relaxation of the prostatic muscles even when minute doses of a specific inhibitor are administered, with no appreciable effects in other organ strips, in particular vessels, being observed. Therefore, they have an excellent efficiency in the treatment of prostatic diseases.

Therefore, the subject matter of the invention is the use of specific inhibitors of sPDE I, sPDE IV and sPDE V in the prophylaxis and treatment of prostatic diseases, in particular benign prostatic hyperplasia, the so-called urge symptoms, pollacuria (frequent micturition), nycturia (nocturnal micturition), weakened urine jet, urge incontinence (involuntary discharge of urine), prostatism, instabilities of the bladder muscles, impotence, and the use of the inhibitors for the preparation of medicaments useful for this purpose as well as medicaments containing sPDE I, IV and V inhibitors for the objects mentioned.

Preferred selective inhibitors of PDE I, IV and V are:

a) 2-(2-propoxyphenyl)-8-azapurin-6-one (zaprinast);

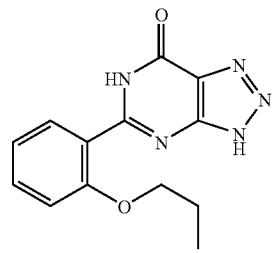

b) dipyridamole;

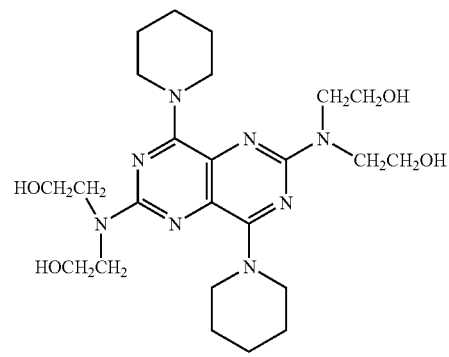

c) 1-(3-chlorophenylamino)-4-phenylphthalazine (MY5445);

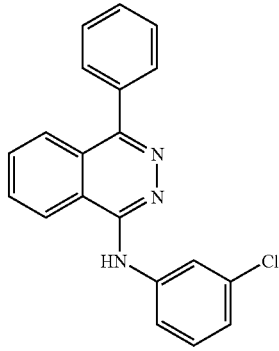

d) 2-(N-(4-carboxypiperidine)-6-chloro-4-(3,4-(methylendioxy)benzyl)amino)quinazoline (E 4021, ER 21355);

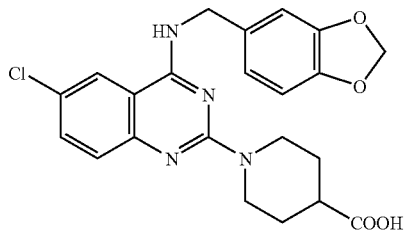

e) 2,3-dihydro-8-hydroxy-7-nitro-1,4-benzodioxine-2-methanol, alpha-nitrate (E 4701);

f) 4-((3,4-(methylendioxy)benzyl)amino)-6,7,8-trimethoxy-quinazoline;

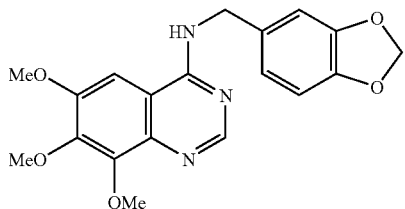

g) 1-methyl-3-propyl-6-(5-(N-(4-methylmorpholino)sulfonyl)-2-ethoxyphenyl)pyrazole[4,5]pyrimidin-4(5H)one (Sildenafil);

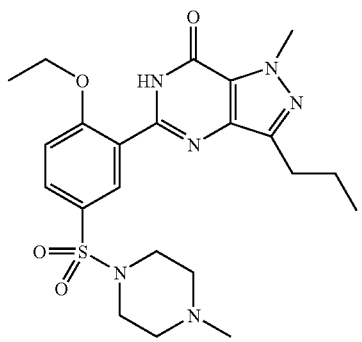

h) 2-n-butyl-5-chloro-1-(2-chlorobenzyl)-4-methylacetate-imidazole;

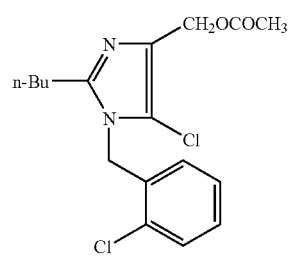

i) 1-cyclopentyl-3-methyl-6-(4-pyridinyl)pyrazolo(3,4-d)pyrimidin-4(5H)-one (WIN 58237);

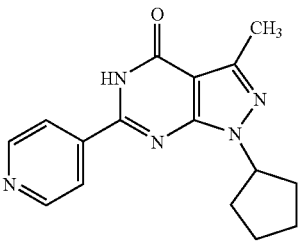

j) 7-(3-(4-acetyl-3-hydroxy-2-propyl-phenoxy)-2-hydroxy-propoxy)-2-carboxy-2,3-didehydro-chronan-4-one (FPL-55712);

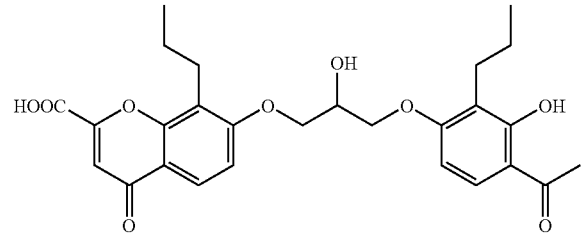

k) quinazolines and their trimethoxy derivatives;
l) pyrazolopyrimidones;
as well as pharmacologically compatible salts thereof.

The pharmacologically compatible salts are obtained in a similar manner by neutralizing the bases with inorganic or organic acids. As the inorganic acids, there may be used, for example, hydrochloric acid, sulfuric acid, phosphoric acid or hydrobromic acid, and as the organic acids, for example, carboxylic, sulfo or sulfonic acids, such as acetic acid, tartaric acid, lactic acid, propionic acid, glycolic acid, malonic acid, maleinic acid, fumaric acid, tannic acid, succinic acid, alginic acid, benzoic acid, 2-phenoxybenzoic acid, 2-acetoxybenzoic acid, cinnamic acid, mandelic acid, citric acid, malic acid, salicylic acid, 3-aminosalicylic acid, ascorbic acid, embonic acid, nicotinic acid, isonicotinic acid, oxalic acid, amino acids, methane-sulfonic acid, ethanesulfonic acid, 2-hydroxyethanesulfonic acid, ethane-1,2-disulfonic acid, benzenesulfonic acid, 4-methyl-benzenesulfonic acid, or naphthalene-2-sulfonic acid.

In the preparation of the medicaments for the treatment of the diseases mentioned, an effective amount of the inhibitors of sPDE I, IV or V or of the salts thereof is used in addition to the usual excipients, vehicles and additives. The dosage depends on the species, body weight, age, individual condition, and kind of administration.

Possible dosage forms are oral, intravenous, transdermal, subcutaneous and intravesicular formulations. The latter are, in particular, those solutions and formulations which are also used for parenteral administration.

Formulations for parenteral administration will contain from 0.15 µg to 1 mg, preferably from 5 to 500 µg, of the compounds mentioned per unit dose and may be present in separate unit dose forms, such as ampoules or vials. Preferably, solutions of the active ingredient are used, more preferably aqueous solutions, and mainly isotonic solutions, but also suspensions. These injection forms may be provided as a ready preparation, or they may be formulated only immediately before use by admixing the active compound, for example, the lyophilizate, optionally together with other solid carriers, with the solvent or suspension medium desired.

For oral administration, there are used the usual galenic preparations, such as tablets, coated tablets, capsules, dispersible powders, granules, aqueous or oily suspensions, syrups, liquors or drops.

Solid preparations may contain inert excipients and vehicles, such as calcium carbonate, calcium phosphate, sodium phosphate, lactose, starch, mannitol, alginates, gelatin, guar gum, magnesium or aluminium stearate, methylcellulose, talcum, highly dispersed silicic acids, silicone oil, higher-molecular fatty acids (such as stearic acid), agar-agar, or vegetable or animal fats and oils, solid high-molecular polymers (such as polyethylene glycol); formulations useful for oral administration may optionally contain additional flavoring and/or sweetening agents.

Liquid preparations may be sterilized and/or may optionally contain additives, such as preservatives, stabilizers, wetting agents, penetration agents, emulsifiers, spreading agents, solubilizers, salts for adjusting the osmotic pressure or for buffering, and/or viscosity modifiers.

Such additives are, for instance, tartrate and citrate buffers, ethanol, complexing agents (such as ethylenediaminetetraacetic acid and its non-toxic salts). For adjusting the viscosity, there may be used high-molecular polymers, such as, for example, liquid polyethylene oxide, carboxymethylcelluloses, polyvinylpyrrolidones, dextranes, or gelatin. Solid vehicles are, for instance, starch, lactose, mannitol, methylcellulose, talcum, highly dispersed silicic acids, higher-molecular fatty acids (such as stearic acid), gelatin, agar-agar, calcium phosphate, magnesium stearate, animal and vegetable fats, solid high-molecular polymers (such as polyethylene glycol).

Oily suspensions for parenteral or topical (in this case intra-vesicular) administrations may contain vegetable, synthetic or semisynthetic oils, such as, for instance, liquid fatty acid esters having from 8 to 22 carbon atoms in the fatty acid chains, for example, palmitic, lauric, tridecylic, margaric, stearic, arachic, myristic, behenic, pentadecylic, linolic, elaidic, brassidic, erucic or oleic acids, which may be esterified with monohydric to trihydric alcohols having from 1 to 6 carbon atoms, such as for instance, methanol, ethanol, propanol, butanol, pentanol, or isomers thereof, glycol, or glycerol. Such fatty acid esters are, for instance, commercially available miglyols, isopropyl myristate, isopropyl palmitate, isopropyl stearate, PEG 6-caprylic acid, caprylates/caprates of saturated fatty alcohols, polyoxyethyleneglycerol trioleates, ethyl oleate, waxy fatty acid esters, such as synthetic duck uropygial fat, coconut oil fatty acid isopropyl ester, oleic acid oleyl ester, oleic acid decyl ester, lactic acid ethyl ester, dibutyl phthalate, adipic acid diisopropyl ester, polyol fatty acid ester, etc. Also useful are silicone oils of various viscosities or fatty alcohols, such as isotridecyl alcohol, 2-octyldodecanol, cetylstearyl alcohol or oleyl alcohol, fatty acids, such as oleic acid. Further, vegetable oils, such as castor oil, almond oil, olive oil, sesame oil, cottonseed oil, peanut oil or soybean oil, may be used. The materials mentioned have the additional property of a spreading agent, i.e. there will be a particularly good spreading on the skin.

As solvents, gelling agents and solubilizers, there may be used water or water-miscible solvents. Useful are alcohols, for example, such as ethanol or isopropyl alcohol, benzyl alcohol, 2-octyldodecanol, polyethyleneglycols, phthalates, adipates, propylene glycol, glycerol, dipropylene or tripropylene glycol, waxes, methylcellosolve, cellosolve, esters, morpholines, dioxane, dimethylsulfoxide, dimethylformamide, tetrahydrofurane, cyclohexanone, etc.

As film-forming agents, there may be, used cellulose ethers which can dissolve or swell both in water and in organic solvents and will form a kind of film after drying, such as hydroxypropyl-cellulose, methylcellulose, ethylcellulose, or soluble starches. Mixed gelling and film-forming agents are also possible by all means. In this case, there are chiefly used ionic macromolecules, such as sodium carboxymethylcellulose, polyacrylic acid, poly-1-methacrylic acid, and salts thereof, sodium amylopectine semi-glycolate, alginic acid or propylene glycol alginate as the sodium salt, gum arabic, xanthan gum, guar gum or carrageen.

As additional formulation aids, there may be used: glycerol, paraffins having different viscosities, triethanolamine, collagen, allantoin, novantisolic acid, perfume oils.

The use of surfactants, emulsifiers or wetting agents may also be required for the formulation, such as, for example, sodium lauryl sulfate, fatty alcohol ether sulfates, disodium N-lauryl β-iminodipropionate, polyoxyethylated castor oil, or sorbitan monooleate, sorbitan monostearate, cetyl alcohol, lecithin, glycerol monostearate, polyoxyethylene stearate, alkylphenol polyglycol ether, cetyltrimethylammonium chloride, or monoalkyl/dialkyl polyglycol ether ortho-phosphoric acid monoethanolamine salts.

Stabilizers, such as montmorillonites or colloidal silicic acids, for the stabilization of emulsions or for preventing decomposition of active substances, such as antioxidants, for example, tocopherols or butylhydroxyanisol, or preservatives, such as p-hydroxybenzoic acid ester, may also be required for the preparation of the formulations desired.

For promoting penetration, intravesicular formulations preferably contain highly compatible organic solvents, such as ethanol, methylpyrrolidone, polyethylene glycol, oleyl alcohol, octanol, linolic acid, triacetin, propylene glycol, glycerol, solketal, or dimethylsulfoxide.

The preparation, filling and sealing of the preparations is done under the usual antimicrobial and aseptic conditions. Also for topical or transdermal application, the preparations are preferably packed in separate unit doses for easy handling, and if required for stability reasons, as with parenteral forms, also by separately packing the active ingredients or their combinations as lyophilizates, optionally with solid carriers, and the solvents required etc.

EXAMPLE 1

Injection

Fifty milligrams of sildenafil is dissolved in distilled water together with 750 mg of NaCl, the pH is adjusted to 3.7 with 1N HCl, distilled water is added to give a total of 100 ml, and the solution is packed in 0.5 ml ampoules.

EXAMPLE 2

Solution for Topical Administration

From 500 mg of sildenafil, 2 ml of isopropyl myristate and 10 ml of ethanol, a solution for topical administration is prepared and packed in unit doses of 2 ml each.

The effectiveness of the medicaments according to the teaching of the invention is demonstrated by the following pharmacological studies:

Human prostatic tissue freshly collected in the course of an operation is cut into small strips (about 3×3×6 mm). The latter are then installed in a bath containing a nutrient solution ensuring survival of the organic strips. By coupling the organic strips to a measuring element, length and force changes of the organic strip can be recorded, and thus actions of medicaments added to the organ bath nutrient solution can be examined through the length and force changes (increase or decrease) of the organic strip. At the beginning of the experiment, the organic strips are contracted with an appropriate standard medicament (e.g., carbachol). After the contraction of the organic strips is completed, an inhibitor of a specific phosphodiesterase is now added in incremental dosage ($10^{-8}$, $10^{-7}$, $10^{-6}$ etc. mol/l) to the organ bath solution, and the relaxation triggered thereby is measured. The results obtained are essentially applicable to the whole organism since human tissue had been used and the metabolic processes studied proceed faster in the whole organism and thus the medicaments will act still more quickly. In these studies, the inhibitors of PDE I, Iv and V proved to have the strongest prostatic tissue relaxing effect.

The proof of whether a compound is suitable for the purpose according to the invention, i.e. is an inhibitor of sPDE I, IV or V, is furnished by known methods, such as described e.g., by Galwan et al.; Arch. Pharmacol. 1990, 342, 221-227; or Nicholson, Br. J. Pharmacol. 1989, 79, 889-897; for example, according to the following general procedure:

Fresh tissue obtained during an operation is homogenized and then ultracentrifuged. Next, the supernatant is filtered, pipetted off and chromatographed. The determination of sPDE is performed as described in M. Truss et al.: Urology 45(5): 893-901, 1995. The determination of the amount of radioactivity permits calculation the enzyme activity in pmol/ml×min. A plot of the activity curve allows to identify fractions in which the phosphodiesterase activity is particularly high. The phosphodiesterase activity of each peak exhibits a different composition with respect to the activity of the different substrates. This special composition of the phosphodiesterase activity allows for the assignment to a specific phosphodiesterase (sPDE). A substance is considered an inhibitor of an sPDE if the concentration thereof which is necessary for inhibiting 50% of the substrate hydrolysis ($IC_{50}$) is at least 20 times lower in the respective peak fraction containing the specific phosphodiesterase than in other peak fractions. For this purpose, enzyme preparations are again prepared, as described above. Now, however, the compound to be tested is added prior to the incubation of the enzyme mixtures according to peak fractions. Then, renewed determination and plotting of the enzyme activity allows to identify a substance as being an inhibitor of the specific phosphodiesterase according to the above-mentioned definition.

The invention claimed is:

1. A method of treating a prostatic disease selected from the group consisting of benign prostatic hyperplasia and prostatism, comprising administering a selective inhibitor of phosphodiesterase IV and/or phosphodiesterase V to a subject having said prostatic disease selected from the group consisting of benign prostatic hyperplasia and prostatism, wherein said inhibitor is selected from the group consisting of:
   a) 2-(N-(4-carboxypiperidine)-6-chloro-4-(3,4-(methylendioxy)benzyl)amino)quinazoline;
   b) 2,3-dihydro-8-hydroxy-7-nitro-1,4-benzodioxine-2-methanol, alpha-nitrate;
   c) 4-((3,4,-(methylendioxy)benzyl)amino)-6,7,8-trimethoxy-quinazoline;
   d) 1-[[3-(4,7-dihydro-1-methyl-7-oxo-3-propyl-1H-pyrazolo[4,3-d]pyrimidin-5-yl)-4-ethoxyphenyl]sulfonyl]-4-methylpiperazine;
   e) 2-n-butyl-5-chloro-1-(2-chlorobenzyl) 4-methylacetate-imidazole; and
   f) 1-cyclopentyl-3-methyl-6-(4-pyridinyl)pyrazolo(3,4-d)pyrimidin-4(5H)-one;
   and whereby said administration treats said prostatic disease selected from the group consisting of benign prostatic hyperplasia and prostatism.

2. The method of claim 1, wherein said inhibitor is administered as part of a composition further comprising a pharmacologically acceptable excipient.

3. A method of relaxing prostatic muscles comprising administering to an individual having benign prostate hyperplasia or lower urinary tract symptomology a selective inhibitor of phosphodiesterase (PDE) IV and/or phosphodiesterase (PDE) V, wherein said inhibitor is selected from the group consisting of:
   a) 2-(2-propoxyphenyl)-8-azapurin-6-one;
   b) dipyridamole;
   c) 2-(N-(4-carboxypiperidine)-6-chloro-4-(3,4-(methylendioxy)benzyl)amino)quinazoline;
   d) 2,3-dihydro-8-hydroxy-7-nitro-1,4-benzodioxine-2-methanol, alpha-nitrate;
   e) 4-((3,4,-(methylendioxy)benzyl)amino)-6,7,8-trimethoxy-quinazoline;
   f) 1-[[3-(4,7-dihydro-1-methyl-7-oxo-3-propyl-1H-pyrazolo[4,3-d]pyrimidin-5-yl)-4-ethoxyphenyl]sulfonyl]-4-methylpiperazine;
   g) 2-n-butyl-5-chloro-1-(2-chlorobenzyl) 4-methylacetate-imidazole;
   h) 1-cyclopentyl-3-methyl-6-(4-pyridinyl)pyrazolo(3,4-d)pyrimidin-4(5H)-one; and
   i) 7-(3-(4-acetyl-3-hydroxy-2-propyl-phenoxy)-2-carboxy-2,3-didehydrochronan-4-one;
   and whereby said administration relaxes prostatic muscles in said individual.

4. The method of claim 3, wherein said inhibitor is administered in a unit dose form.

5. The method of claim 3, comprising administering a composition comprising said inhibitor, wherein said composition is administered in a unit dose form.

* * * * *